(12) United States Patent
Fitts et al.

(10) Patent No.: US 7,678,138 B2
(45) Date of Patent: Mar. 16, 2010

(54) TWO PIECE CROSS-PIN GRAFT FIXATION

(75) Inventors: Steven E. Fitts, Ridge Manor, FL (US);
Wamis Singhatat, Santa Ana, CA (US);
Drew Powell Amery, Clearwater, FL (US)

(73) Assignee: Linvatec Corporation, Largo, FL (US)

( * ) Notice: Subject to any disclaimer, the term of this patent is extended or adjusted under 35 U.S.C. 154(b) by 576 days.

(21) Appl. No.: 10/438,510

(22) Filed: May 15, 2003

(65) Prior Publication Data

US 2003/0216780 A1 Nov. 20, 2003

Related U.S. Application Data

(60) Provisional application No. 60/380,376, filed on May 15, 2002, provisional application No. 60/423,022, filed on Nov. 1, 2002.

(51) Int. Cl.
*A61B 17/56* (2006.01)
(52) U.S. Cl. .................. 606/300; 623/13.12
(58) Field of Classification Search .......... 606/59, 606/60, 72–73, 232, 148; 623/13.11–13.2
See application file for complete search history.

(56) References Cited

U.S. PATENT DOCUMENTS

| | | | |
|---|---|---|---|
| 5,004,474 A | 4/1991 | Fronk et al. | |
| 5,266,075 A | 11/1993 | Clark et al. | |
| 5,306,301 A * | 4/1994 | Graf et al. | 606/72 |
| 5,350,380 A | 9/1994 | Goble et al. | |
| 5,354,300 A | 10/1994 | Goble et al. | |
| 5,372,599 A * | 12/1994 | Martins | 606/75 |
| 5,393,302 A * | 2/1995 | Clark et al. | 606/72 |
| 5,397,356 A | 3/1995 | Goble et al. | |
| 5,431,651 A | 7/1995 | Goble | |
| 5,562,671 A | 10/1996 | Goble et al. | |
| 5,601,562 A * | 2/1997 | Wolf et al. | 606/86 |
| 5,643,266 A * | 7/1997 | Li | 606/72 |
| 5,674,224 A | 10/1997 | Howell et al. | |
| 5,688,284 A | 11/1997 | Chervitz et al. | |
| 5,707,395 A * | 1/1998 | Li | 606/232 |
| 5,871,504 A * | 2/1999 | Eaton et al. | 606/232 |
| 5,895,425 A | 4/1999 | Grafton et al. | |
| 5,918,604 A | 7/1999 | Whelan | |
| 6,066,173 A | 5/2000 | McKernan et al. | |
| 6,086,591 A * | 7/2000 | Bojarski | 606/64 |
| 6,113,604 A | 9/2000 | Whittaker et al. | |
| 6,132,433 A | 10/2000 | Whelan | |

(Continued)

*Primary Examiner*—Eduardo C Robert
*Assistant Examiner*—Mary Hoffman
(74) *Attorney, Agent, or Firm*—Gene Warzecha (57) ABSTRACT

In one aspect of the invention, a cross-pin includes a distal portion having an axis, a distal end, and a proximal end. A proximal cylindrical portion includes a threaded exterior surface. A junction may be interposed between the distal and proximal portions to enable the proximal portion to rotate relative to the distal portion. In another aspect of the invention, a graft retaining system for retaining a graft in a bone tunnel includes a graft block having a proximal end and a distal end, and sized to fit within the bone tunnel. A cross pin transverse to the bone tunnel attaches the graft block adjacent the tunnel. An intermediate connector is attached to the graft block at a point distal to the cross pin and connects the graft to the graft block so as to apply compressive forces to the graft block.

27 Claims, 4 Drawing Sheets

U.S. PATENT DOCUMENTS

| | | | |
|---|---|---|---|
| 6,152,928 A * | 11/2000 | Wenstrom, Jr. | 606/72 |
| 6,245,073 B1 * | 6/2001 | Conteduca et al. | 606/72 |
| 6,264,694 B1 * | 7/2001 | Weiler | 623/13.14 |
| 6,273,890 B1 * | 8/2001 | Frazier | 606/73 |
| 6,306,138 B1 | 10/2001 | Clark et al. | |
| 6,387,129 B2 * | 5/2002 | Rieser et al. | 623/13.14 |
| 6,440,134 B1 * | 8/2002 | Zaccherotti et al. | 606/62 |
| 6,562,043 B1 * | 5/2003 | Chan | 606/65 |
| 6,712,849 B2 * | 3/2004 | Re et al. | 623/13.14 |
| 6,887,259 B2 * | 5/2005 | Lizardi | 606/232 |
| 7,063,724 B2 * | 6/2006 | Re et al. | 623/13.14 |
| 7,097,654 B1 * | 8/2006 | Freedland | 606/232 |
| 2005/0267479 A1 * | 12/2005 | Morgan et al. | 606/73 |

* cited by examiner

TWO PIECE CROSS-PIN GRAFT FIXATION

CROSS-REFERENCE TO RELATED APPLICATIONS

This application claims the benefit of U.S. Provisional Application No. 60/380,376, filed May 15, 2002, and U.S. Provisional Application No. 60/423,022 filed Nov. 01, 2002.

FIELD OF THE INVENTION

The invention relates to soft tissue repair and reconstruction. More particularly, the invention relates to the fixation of a graft within a bone tunnel. Still more particularly, the invention relates to improvements in the use of a transverse pin to retain a graft within a bone tunnel.

DESCRIPTION OF THE PRIOR ART

The repair and reconstruction of torn or damaged soft tissues is a common surgical procedure. For example, replacement graft ligaments may be secured at the site of the original ligament. The procedure generally involves drilling bone tunnels into adjacent bones at the site of the original ligament and securing within these bone tunnels a graft ligament. In many applications, such as in the knee joint, such procedures may be performed arthroscopically. The graft ligament may be an autograft, an allograft, a xenograft, and/or it may be totally artificial and synthetic. The most common types of graft ligaments include ones which may be bone-tendon-bone or soft tissue (such as semitendinosus and gracilis tendons), both types harvested by techniques well known to those skilled in the art.

The graft ligaments are secured within the bone tunnels in a variety of ways. Of prime importance is the degree to which they can withstand pullout forces prior to complete healing. For example, it is known to use interference screws inserted parallel to the tunnel axis to compress the ends of the graft ligament against the walls of the bone tunnel to secure the graft ligament and promote tissue in-growth.

Recently, cross-pin fixation devices have been developed to retain the graft ligament within the bone tunnel by securing it with a pin extending transversely through the tunnel and the ligament. Cross-pin fixation, although a more complex procedure, generally provides the highest pullout forces.

Various methods are known to achieve cross-pin fixation. All methods require the initial formation of the ligament bone tunnel in the tibia and femur in a conventional manner. All methods also end up with a pin situated transversely through the graft ligament. (As used herein, (1) in the case of a bone-tendon-bone graft, "through" means actually through the bone at one end of the graft and (2) in the case of a soft tissue graft, "through" means the graft ligament is folded over on itself and the pin extends between the folded ligament strands.) The differences between the various cross-pin fixation methods lies primarily in the manner in which the graft ligament is engaged with the cross-pin. One method utilizes bone-tendon-bone grafts and involves pushing or pulling one of the bone ends of the graft into the femoral tunnel and drilling a transverse hole in the femur to place a cannulated pin directly and transversely through the bone end. U.S. Patents representative of this method include the following: U.S. Pat. No. 5,004,474 (Frank et al.); U.S. Pat. Nos. 5,350,380, 5,354,300, 5,397,356, 5,431,651 (FIGS. 7, 7A), U.S. Pat. No. 5,562,671 (all to Goble et al.); U.S. Pat. No. 5,688,284 (Chervitz et al.); U.S. Pat. No. 6,066,173 (McKernan et al.) and U.S. Pat. No. 6,113,604 (Whittaker et al.).

This method may be further understood by reference to aforementioned U.S. Pat. No. 5,350,380 (Goble et al.) which shows a bone drill for drilling a ligament bone tunnel from the proximal tibial surface into the femur. The bone drill is used in conjunction with a C-shaped drill guide to position the location of a transverse hole to be drilled through the lateral femoral surface in order to intersect the ligament bone tunnel at a predetermined location. The graft is pulled into the ligament bone tunnel by sutures extending through the tunnel and a tapered transverse pin is screwed into place to secure the graft.

Another method utilizes soft tissue grafts and involves folding the strands of graft material to create a bundle and pushing the bundle into the femoral tunnel. A cannulated guide pin is placed through the graft ligament strands (i.e. at the fold). U.S. Patents representative of this method are U.S. Pat. No. 5,601,562 (Wolf et al.) and U.S. Pat. No. 6,306,138 (Clark et al.)

This method may be further understood by reference to aforementioned U.S. Pat. No. 5,601,562 (Wolf et al.) which discloses a way of pushing a soft tissue graft ligament into a bone tunnel using a notched ligament inserter. A guide wire is then drilled transversely through one of the pair of notches on the inserter to enable a guide pin to be situated within the loop formed by the soft tissue graft. A cannulated cylindrical cross-pin implant is placed over the guide pin and advanced through the transverse tunnel and into the femur on the opposite side of the tunnel to complete the fixation.

Another method also utilizes soft tissue grafts but requires attaching a suture to one end of the graft, placing a loop of the suture in the bone tunnel at the site wherein the transverse pin will be placed, advancing a transverse guide wire or pin through the loop of suture and then pulling or threading the graft over the pin or guide wire (if the latter, then advancing a cannulated pin over the guide wire) to form a fold in the graft ligament. U.S. Patents representative of this method are: U.S. Pat. Nos. 5,266,075 and 5,393,302 (both to Clark et al.); U.S. Pat. No. 5,431,651 (FIG. 7B, 7C to Goble); and U.S. Pat. No. 5,674,224 (Howell et al.).

The method may be further understood by reference to aforementioned U.S. Pat. No. 5,393,302 (Clark et al.) which discloses a method of inserting a soft tissue graft ligament by pushing it into the bone tunnel on a tendon threader having orthogonally oriented slots at its distal end. One pair of opposed slots engages the graft ligament (or suture secured to the graft ligament) in order to position it at the end of the ligament bone tunnel. A transverse pin may then be drilled directly through the other set of opposed slots. The graft ligament can then be looped over the transverse pin.

Another method also utilizes soft tissue grafts but requires a transverse tunnel entirely through the femur at a point intersecting the ligament bone tunnel. A flexible guide wire is placed in the transverse tunnel and its middle portion is pulled out of the ligament bone tunnel entrance forming a guide wire loop. The soft tissue graft ligament is passed through the guide wire loop and folded back on itself. By pulling in opposite directions on the ends of the flexible guide wire, the graft is pulled into place. The guide wire is then used to guide a cannulated cross-pin into place under the graft ligament fold. U.S. Patents representative of this method are U.S. Pat. No. 5,895,425 (Grafton et al.) and U.S. Pat. Nos. 5,918,604 and 6,132,433 (both to Whelan). This method may be further understood by reference to aforementioned U.S. Pat. No. 5,895,425 (Grafton et al.) which shows that, after the formation of the ligament bone tunnel, a transverse bone tunnel is formed entirely through the femur intersecting the end of the ligament bone tunnel at which the graft is to be placed. A flexible guide wire is threaded through this transverse bone tunnel. The central portion of this flexible guide wire is pulled out of the ligament bone tunnel until it is completely outside the body. A soft tissue ligament graft is looped around this flexible guide wire. The ends of the flexible guide wire are then pulled away from each other to draw the flexible guide wire and the looped graft ligament into the ligament bone tunnel. A cannulated transverse pin is then drilled into place across the ligament bone tunnel and the flexible guide wire is withdrawn.

It is also known that the transverse pin need not be exactly perpendicular to the ligament bone tunnel. U.S. Pat. No. 5,688,284 (Chervitz et al.) shows, for example, a variable angle drill guide which enables the transverse pin to be oriented at a desired angle relative to the ligament bone tunnel.

U.S. Pat. No. 6,066,173 (McKeman et al.) shows another method of cross-pinning fixation utilizing a plurality of transverse pins inserted through the ligament within the ligament bone tunnel.

All known cross-pin fixation systems have some disadvantages and it is an object of this invention to overcome these disadvantages. In the case of the first three methods it is difficult and time consuming to place the transverse pin and thread the graft ligament over the cross-pin or guide pin. In the case of the last method, pulling in opposite directions to move a graft perpendicular to the pulling directions is difficult and the flexible guide wire can be kinked or severed by the cross-pin. In the methods involving pushing the graft ligament into place, the diameter of the ligament bone tunnel must be larger than desired in order to accommodate the dimensions of the pusher and the graft ligament such that when the pusher is removed, the bone tunnel is over-sized relative to the graft.

SUMMARY

The present invention provides a system for cross-pin fixation of a graft in a bone tunnel.

In one aspect of the invention a graft retaining system for retaining a graft in a bone tunnel comprises a graft block having a proximal end, a distal end, and a longitudinal axis extending therebetween, the block being sized to fit within the bone tunnel; an intermediate connector connecting a predetermined portion of the graft and a predetermined portion of the graft block; and means for attaching the graft block adjacent the bone tunnel at a predetermined point along the length of said tunnel, the means for attaching being situated transverse to the axis of said bone tunnel.

In another aspect of the invention a graft retaining system for retaining a graft in a bone tunnel comprises a graft block having a proximal end, a distal end, and a longitudinal axis extending therebetween, the block being sized to fit within the bone tunnel; tunnel attachment means for attaching the graft block adjacent the bone tunnel at a predetermined point along the length of the tunnel, the tunnel attachment means being situated transverse to the axis of the bone tunnel, the tunnel attachment means being located proximally of the distal end of the graft block; and graft attachment means for connecting the graft to the graft block at a position distal to the tunnel attachment means such that tensile forces on the graft result in compressive forces on the graft block between the graft attachment means and the tunnel attachment means.

In another aspect of the invention a graft retaining system for retaining a graft in a bone tunnel comprises a graft block having a generally cylindrical body having a proximal end, a distal end, and a longitudinal axis extending therebetween, the block being sized to fit within the bone tunnel; a transverse pin engageable with the graft block to attach the graft block within the bone tunnel at a predetermined point along the length of the tunnel; and a flexible loop adapted to engage both the graft block and the graft.

In another aspect of the invention a graft retaining system for retaining a graft in a bone tunnel comprises a graft block having a generally cylindrical body having a proximal end, a distal end, and a longitudinal axis extending therebetween, the block being sized to fit within the bone tunnel; a transverse pin engageable with the graft block at a predetermined engagement portion on the graft block to attach the graft block within the bone tunnel at a predetermined point along the length of the tunnel; and at least one channel formed on the graft block distal of the predetermined engagement portion for receiving a portion of the graft such that tensile loading of the graft results in compressive loading of the graft block between the predetermined engagement portion and the transverse pin.

In another aspect of the invention a graft retaining system for retaining a graft in a bone tunnel comprises a graft block having a generally cylindrical body having a proximal end, a distal end, a longitudinal axis extending therebetween, and a pair of opposed longitudinal side surfaces, the block being sized to fit within the bone tunnel; a transverse pin engageable with the graft block at a predetermined engagement portion on the graft block to attach the graft block within the bone tunnel at a predetermined point along the length of the tunnel; a flexible loop adapted to engage both the graft block and the graft; and at least one channel formed on the graft block distal of the predetermined engagement portion for receiving a portion of the flexible loop such that tensile loading of the graft results in compressive loading of the graft block between the predetermined engagement portion and the transverse pin.

In another aspect of the invention a cross-pin comprises a distal portion having an axis, a distal end and a proximal end; a proximal cylindrical portion having an axis, a distal end and a proximal end, aligned with the distal portion, the proximal portion comprising a threaded exterior surface and a driving means; a junction means interposed between the distal and proximal portions, the junction means adapted to enable the proximal portion to rotate about its axis relative to the distal portion to thereby move the proximal portion rotationally and distally while pushing the distal portion distally.

In another aspect of the invention a method for securing a graft in a bone tunnel comprises providing a graft block having a body and an intermediate connector attached to and extending from the body; attaching a graft to the graft block by connecting it to the intermediate connector; providing a transverse member for being received by the graft block; fitting the graft block with attached graft into the bone tunnel; and engaging the transverse member with the graft block transversely across the bone tunnel to fix the location of the graft block within the bone tunnel.

BRIEF DESCRIPTION OF THE DRAWINGS

Various embodiments of the present invention will be discussed with reference to the appended drawings. These drawings depict only illustrative embodiments of the invention and are not to be considered limiting of its scope.

DETAILED DESCRIPTION

Embodiments of a two piece cross-pin graft system include a graft block sized to fit within a bone tunnel and fixation means for fixing the graft block within the bone tunnel. The graft fixation system may be used to attach any appropriate graft including for example supplemental and/or replacement grafts for the soft tissues associated with the skeletal system. For example, the system may be used to replace soft tissues associated with skeletal joints such as the hip, knee, shoulder, wrist, elbow, ankle, vertebral, phalangeal, temporomandibular, and other joints and locations within a body. For example, the graft fixation system may be used to attach, within a bone tunnel, grafts associated with human knee joint tissues such as the anterior cruciate ligament, the posterior cruciate ligament, the medial collateral ligament, and the lateral collateral ligament.

The graft block may be a unitary or multi-piece construction comprising any suitable biocompatible materials. Exemplary materials include metals, polymers, and/or other suitable materials and combinations thereof. For example, the graft block may comprise metals including stainless steels, titanium, titanium alloys, cobalt-chromium steels, nickel-titanium alloys, and/or others. The graft block may comprise nonresorbable polymers including polyolefins, polyesters, polyimides, polyamides, polyacrylates, poly(ketones), fluropolymers, siloxane based polymers, and/or others. The graft block may comprise resorbable polymers including polyesters (e.g. lactide and glycolide), polyanhydrides, poly (aminoacid) polymers (e.g. tyrosine based polymers), and/or others. The graft block may comprise other materials including nonresorbable and resorbable ceramics (e.g. hydroxyapitite, calcium sulfate) or biocompatible glasses.

The graft block includes means for attaching the graft to the block. The means for attaching the graft may include an aperture or channel formed in the graft block for receiving a portion of the graft or an additional intermediate connector. The aperture or channel may include a shielded portion with material overlying the aperture or channel to more fully retain and protect the graft and/or intermediate connector from abrasion with the bone tunnel wall. An intermediate connector can, for example, connect to a portion of the graft block and to a portion of the graft by being looped around or through the graft block or by having the graft block molded to the intermediate connector.

The graft and/or intermediate connector may contiguously connect to the graft block distally of the fixation means for fixing the graft block within the bone tunnel such that tensile forces on the graft result in compressive forces on the portion of the graft block between the graft and/or intermediate connector and the fixation means. This arrangement eliminates tensile forces on the graft block and prevents tensile breakage of the graft block from being a weak link in the system. In particular, this is helpful where the graft block is made of materials that perform better in compression rather than in tension; e.g. certain ceramics and degradable lactide and/or glycolide based polymers. The present investigators have found that in particular, polylactic acid is stronger, and its strength degrades in a more favorable manner, in vivo when loaded in compression rather than in tension. The intermediate connector may form a loop around a portion of the graft block, for example by being looped through the aperture or channel at the distal end of the graft block and extending beyond the proximal end of the graft block to receive the graft.

The intermediate connector may be flexible to allow it to compress and conform to the graft, graft block, and tunnel so that it can accommodate the smallest possible close fitting tunnel. Likewise, a flexible intermediate connector will distribute the stresses on the graft and graft block for a strong connection. A flexible intermediate connector may be in the form of a flexible member interposed between the graft block and the graft by being, for example, looped through an aperture or channel, having the graft block molded around the intermediate connector, or otherwise. For example, a flexible material may be looped through an aperture and extend beyond the graft block to form a flexible loop for receiving the graft. The intermediate connector may be both flexible and arranged to impart compressive forces on the graft block as described above. A flexible intermediate connector may comprise one or more continuous or closed loops of flexible material or it may comprise a strand of flexible material looped multiple times through or around a portion of the graft block. It may be formed by tying, bonding, otherwise joining, or forming as a single piece. The flexible material may comprise a single piece or a plurality of pieces, such as filaments, that are parallel, twisted, braided, woven, knitted, bonded or otherwise assembled into a cord, tape, fabric, or film.

The intermediate connector may comprise metals, resorbable polymers, nonresorbable polymers, and/or other biocompatible materials. For example, the intermediate connector may comprise non-resorbable materials such as stainless steel, titanium, titanium alloys, cobalt-chrome alloys, polyethylene, polyester, polylactic acid, polytetrafluroethylene, and/or silicone polymers. For example, the intermediate connector may comprise high strength polyethylene fiber. The intermediate connector may also comprise resorbable materials such as polylactic acid, polyglycolic acid, caprolactone, and/or polyamino acid polymers.

The graft block may also include means for passing the graft block longitudinally along the bone tunnel. The means for passing may include means for pushing and or pulling the graft block along the bone tunnel. For example, the graft block may be pushed with a rigid shaft engageable with the graft block. The graft block may be pulled with a rigid or flexible member engageable with the graft block. For example the graft block may include an aperture receiving a passing suture that is pulled from the opposite end of the bone tunnel. The graft block may also include means for aligning the graft block in a predetermined orientation within the bone tunnel, for example, in order to align with a transverse aperture to receive a transverse member to fix the graft block at a desired longitudinal position in the bone tunnel. One example of a means for aligning the graft block includes a keyway formed in the graft block for engaging a rotationally rigid member in a known rotational relationship such as a rigid shaft shaped to fit a slot to maintain the graft block in known rotational alignment with the shaft. Another exemplary means for aligning the graft block includes a projection extending radially from the graft block to engage a corresponding slot previously formed in the wall of the bone tunnel at a known circumferential position.

The means for fixing the graft block within the bone tunnel may include an aperture through the graft block and a transverse member engageable with the aperture and the wall of the bone tunnel. For example, the graft block may contain a transverse aperture for receiving a transverse pin extending through the aperture and into the bone on either side of the graft block. The transverse member may be any suitable member for fixing the graft block including a pin, screw, bolt, staple and or other suitable member. It may be smooth or it may have means to help retain it in its position such as ribs, teeth, barbs, threads, and/or an expanding anchor arrangement or other suitable means. It may be inserted by pressing, impacting, rotating, or by other suitable means. For example, the transverse member can be a pin having a smooth first end and a second threaded end; the smooth end being received in the aperture of the graft block and the threads engaging the bone adjacent the bone tunnel. Furthermore, the transverse member may be a unitary construction or a multiple piece construction. For example, the transverse member may comprise a multiple piece cross-pin having a distal portion, a proximal cylindrical portion aligned longitudinally with the distal portion, and a junction between the distal and proximal portions. The junction may be any suitable junction to permit rotation of the proximal portion relative to the distal portion such that the proximal portion can be turned to move the distal portion axially without turning the distal portion. For example, the proximal portion can be threaded and the distal portion can be smooth. Such a cross-pin can be used with a graft block or with a graft alone. One advantage of such a two piece cross-pin is that the lack of rotation of the distal end reduces the likelihood of the distal end being entangled in the graft and/or suture. Another advantage of such a two-piece cross-pin is that the distal end can be made non-cylindrical to fit a non-cylindrical graft block aperture such as may be desirable with small bone tunnels where the graft block size is limited and would admit only a small cylindrical cross-pin. By making the pin non-cylindrical, the pin strength can be increased without the need to increase the graft block aperture diameter.

Figures 1, 2:
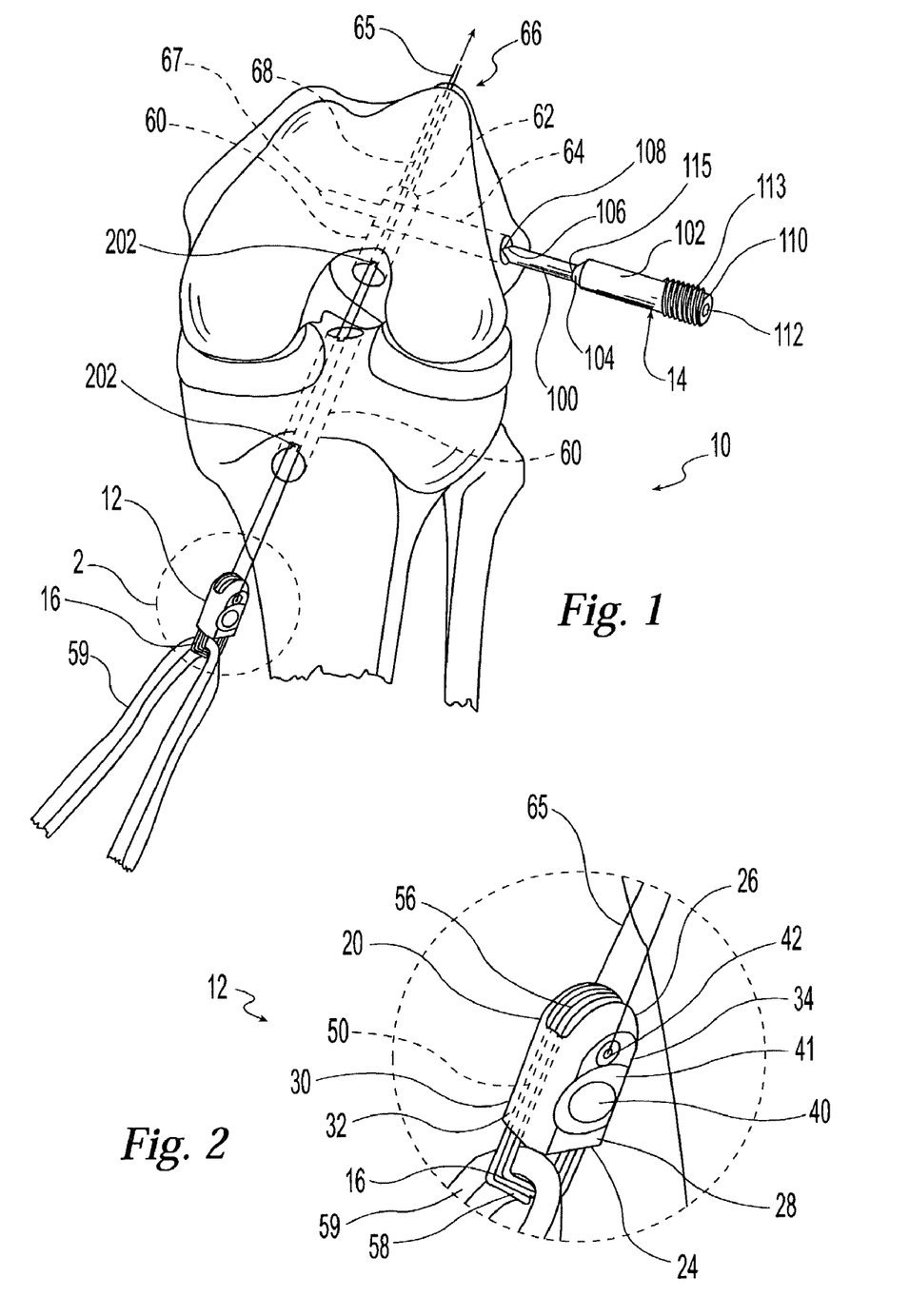
FIG. 1 is a perspective view of a human knee joint showing the insertion of a graft block and cross-pin according to the present invention.
FIG. 2 is a detail view taken from FIG. 1.

FIGS. 1 and 2 illustrate an exemplary graft fixation system in use to replace the anterior cruciate ligament of a human knee. The fixation system 10 comprises a graft block 12, a cross-pin 14 and an intermediate connector in the form of a retaining loop 16. The graft block 12 comprises a body 20 having a proximal end 24 and a distal end 26. The terms "proximal" and "distal" are intended to refer to the orientation of graft block 12 and cross-pin within their respective bone tunnels, the proximal end being closer to the tunnel entrance and the distal end being farther away. The body 20 is a generally rectilinear member having a pair of opposed and parallel planar faces 28 and 30 and a pair of opposed and parallel side faces 32 and 34. The planar side faces 28 and 30 may be used to provide relief areas for passing a suture 65 in the bone tunnel 60. When used in this way, the side faces 28 and 30 need not extend the full length of the body 20 as shown, but may alternatively extend only from the distal end to the smaller aperture 42. Alternatively, instead of opposed planar surfaces, relief for the suture 65 may be provided by a groove or trough extending distally from the smaller aperture 42 on each side of the graft block 12. A large aperture 40 extends transversely through the body 20 between faces 28 and 30. A chamfer 41 extends radially outwardly from the large aperture 40 and provides a tapering transition from the faces 28 and 30 to the large aperture 40. A smaller aperture 42 extends parallel to aperture 40 distally thereof. Body 20 is also provided with a pair of parallel longitudinal channels 50 (one side being shown in hidden line in FIG. 2) extending between the proximal 24 and distal 26 ends to receive a portion of the retaining loop 16 and retain it on the graft block 12. The channels are also covered by the sides 32 and 34 to further retain the loop and protect it from abrasion from the bone tunnel. The loop 16, which may be made of a flexible material, has a distal end 56 lying along distal end 26 of the graft block and a proximal end 58 extending below the proximal end 24 of the body 20 to receive a graft 59 to attach it to the graft block 12. In the illustrative embodiment, the loop comprises multiple strands of a flexible material. Alternatively, the channels 50 may be made large enough to receive the graft 59 directly. In the illustrative embodiment, the loop 16 passes distally over the large aperture 40 and connects the graft 59 proximally of the large aperture such that the portion of the graft block between the loop and the large aperture 40 is placed in compression when the graft is placed in tension.

The side surfaces 32 and 34 may be cylindrical in part. The illustrative graft block 12 may be constructed by milling opposing flat faces 28, 30 on a cylindrical body, molding, sintering, or forming by other suitable methods. The diameter of the graft block body 20 is preferably slightly less than the diameter of the bone tunnel 60 to enable the body 20 to rotate about its axis to facilitate engagement with a cross-pin 14 while maintaining its longitudinal orientation within the tunnel.

The transverse member of this illustrative embodiment comprises a cross-pin 14 having a distal cylindrical section 100, a proximal cylindrical section 102, a tapered transition section 104 between the two cylindrical sections, and a tapered distal end 106 terminating in a pointed distal tip 108. The proximal end 110 of pin 14 is provided with a torque transmitting driver engagement portion such as a recessed, hexagonal drive recess 112. The proximal cylindrical section 102 may be provided with a retention means as previously mentioned. The illustrative embodiment of FIG. 1 includes cancellous screw threads 113 to enable the pin 14 to be advanced into or withdrawn from the femur along its longitudinal axis as it is rotated and to hold its position once it is placed. Alternatively, the cross-pin 14 may have a junction 115 between the proximal 102 and distal 100 sections to permit rotation of the proximal section 102 relative to the distal section 100 such that the proximal section 102 can be turned to drive the distal section 100 while the distal section 100 does not turn.

The diameter of the distal section 100 is approximately equal to the diameter of the large aperture 40 of the graft block 12. The tapered distal end 106 facilitates engagement of the pin with the aperture 40. If the graft block 20 is situated in the tunnel with the aperture axis partially out of alignment with the pin axis, the tapered distal end 106 and the chamfer 41 will engage one another and cause the graft block 12 to rotate about its axis to align the aperture 40 with the pin 14.

In use, a bone tunnel 60 is drilled through the tibia and femur to a predetermined depth. The tunnel drill is then removed and replaced with a guide for guiding a transverse drill to form a transverse hole 64 through the lateral femur intersecting with the bone tunnel 60 and passing into the femur on the opposite side of the tunnel. The transverse hole may be stepped such that it has a smaller distal diameter 67 to correspond to the cross-pin 14 geometry. The transverse drill and the drill guide are then removed. A passing suture 65 is loaded through the smaller aperture 42 of the graft block 12 and attached to a passing pin, such as a K-wire having an eyelet at one end. The passing pin is inserted through the bone tunnel 60 and drilled through the distal end 62 of the bone tunnel, through the femur, out through the anterolateral femoral cortex 66, and adjacent to or through the quadriceps muscle. The graft assembly may be pulled into the bone tunnel by pulling the passing suture through the tunnel 68 thus formed. Because the distal end 62 of bone tunnel 60 ends at a predetermined point the tunnel 60 is sometimes referred to as having a closed end. A continuation of tunnel 68 having a smaller diameter than tunnel 60 does not affect the closed nature of tunnel 60 because the diameters of the respective tunnels do not permit the advancement of the graft block beyond distal end 62. The surgeon only needs to generally align the graft block 12 so that the aperture 40 is in general alignment with the transverse hole 64 prior to passing the graft block 12 into the bone tunnel. Once the graft block is seated in the bone tunnel, the cross-pin 14 is advanced to secure the graft block in the tunnel. Because of the chamfered 41 entrance of the aperture 40 and the taper 106 on the pin 14, the pin 14 can engage the graft block such that even if there is some misalignment the graft block will rotate into alignment with the pin.

Figures 3, 4, 5:
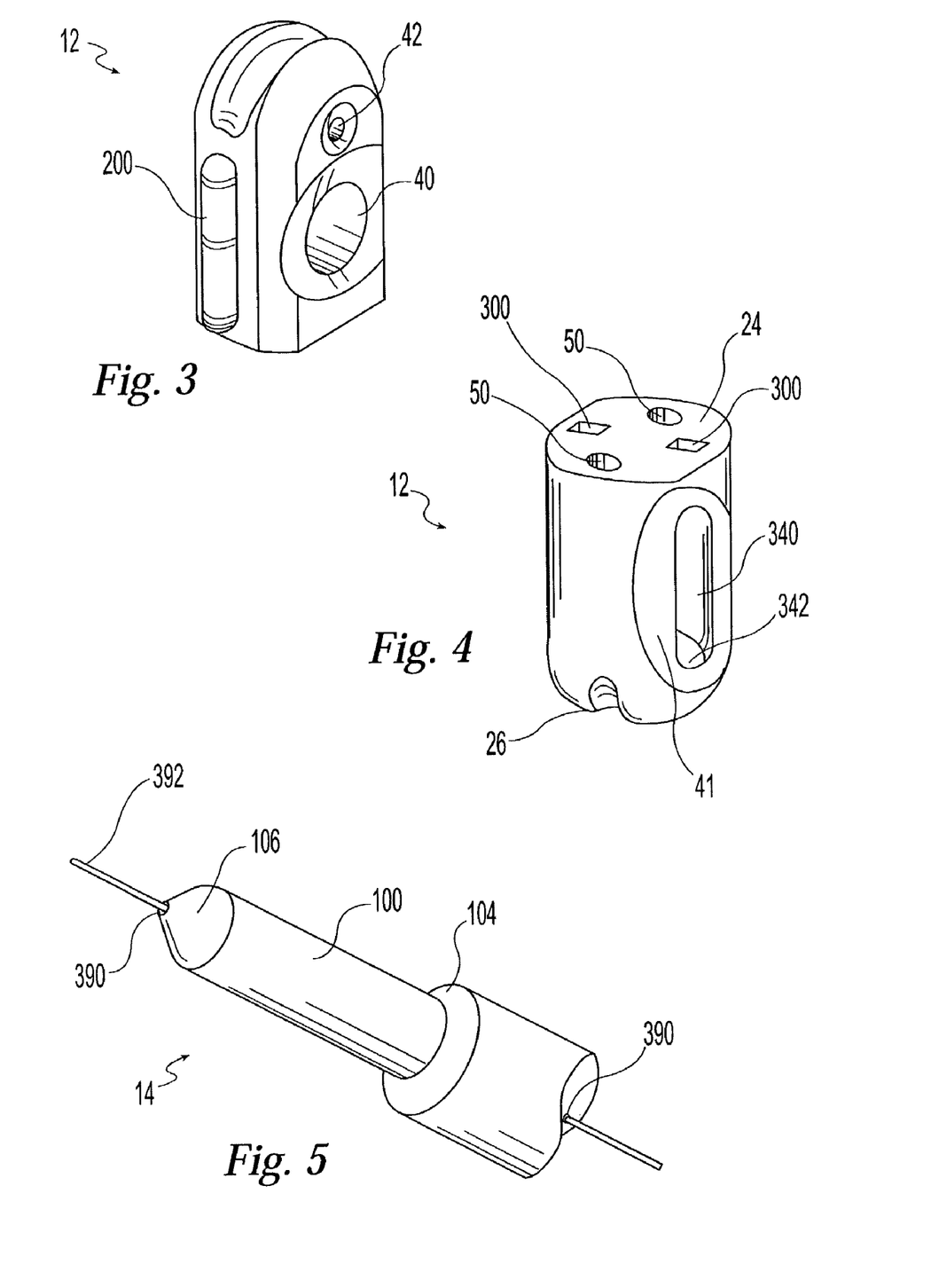
FIG. 3 is perspective view of an alternative embodiment of the graft block of FIG. 1.
FIG. 4 is a perspective view of an alternative embodiment of the graft block of FIG. 1.
FIG. 5 is a perspective view of an alternative embodiment of the cross-pin of FIG. 1.

FIG. 3 illustrates an alternative embodiment of the graft block 12 of FIG. 1 having a longitudinally extending radial projection 200. The projection 200 engages a slot or notch 202 previously formed in the wall of the bone tunnel at a known circumferential position such that the projection 200 is received in the slot 202 as the graft block 12 is inserted into the bone tunnel to align the aperture 40 with the transverse hole 64.

FIG. 4 illustrates an alternative embodiment of the graft block 12 of FIG. 1 having an optional keyway for engaging a rotationally rigid shaft shaped to fit the keyway. The keyway may have one or more openings. In the illustrative embodiment, the keyway comprises a pair of notches 300 that are adapted to receive a forked inserter which has a gap between the forks to accommodate the graft and/or intermediate connector. The engagement of the shaft and keyway maintains the graft block 12 in known rotational alignment with the shaft so that the shaft can be positioned to properly align the graft block 12 with the transverse hole 64. The illustrative embodiment of FIG. 4 also depicts an optional longitudinally elongated aperture 340. Such an elongated aperture may be useful, for example, in a small diameter bone tunnel to facilitate a transverse member having a corresponding non-cylindrical cross-section to increase the strength of the transverse member without requiring a larger graft block diameter. For example, the cross-pin 14 of FIG. 1 may be made with a non-cylindrical distal section 100. This may be advantageously combined with the above described alternative cross-pin having a rotating junction between the proximal 102 and distal 100 sections. In this way, the proximal end 102 may be rotated while the non-cylindrical distal section progresses without rotation. Alternatively, a non-cylindrical cross-pin may be impacted or pressed into position. The non-cylindrical aperture of FIG. 4 may also be used with a transverse member having a round cross-section to permit the transverse member to engage the graft block even when there is some longitudinal misalignment of the graft block 12 with the transverse hole 64. The transverse member may pass through the aperture 340 proximal to the distal end 342 of the aperture. If so, when the graft is tensioned, the graft block will be pulled proximally until the distal end 342 engages the transverse member. The aperture 340 is chamfered 41 to also permit some rotational misalignment as described above.

FIG. 5 illustrates an alternative embodiment of the cross-pin 14 of FIG. 1 having an optional longitudinal cannula 390 to permit the cross-pin 14 to follow a guide wire 392 if desired.

Figure 6:
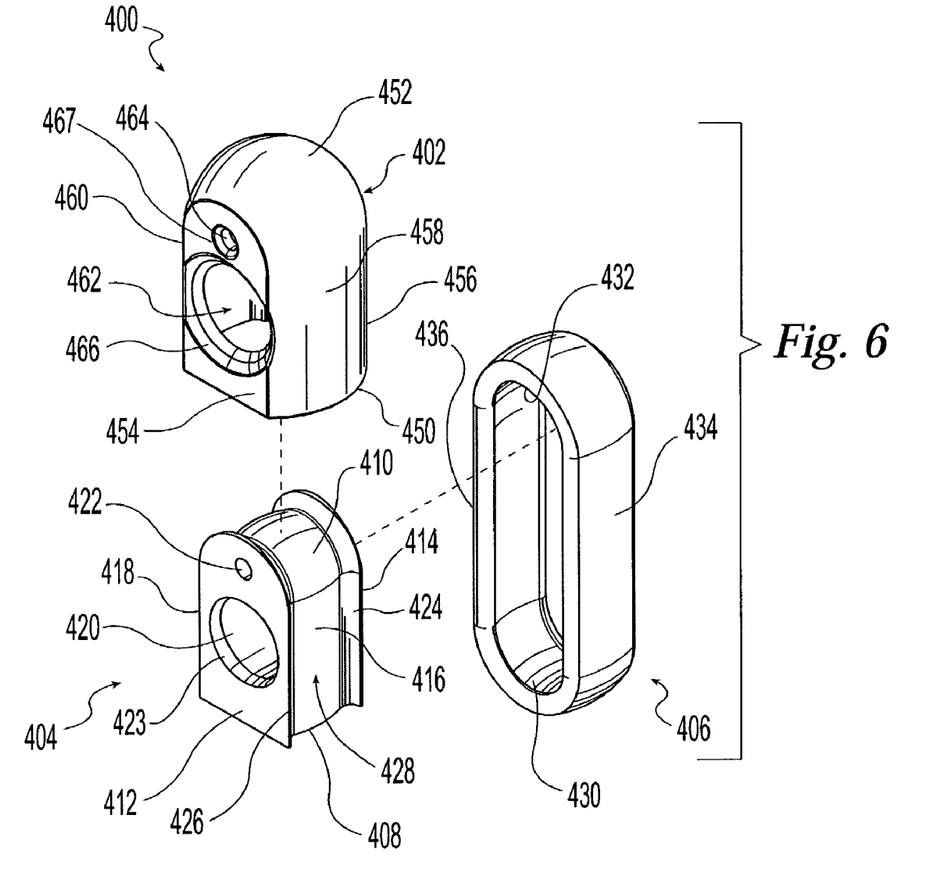
FIG. 6 is an exploded perspective view of an alternative embodiment of the graft block of FIG. 1.
Figure 7:
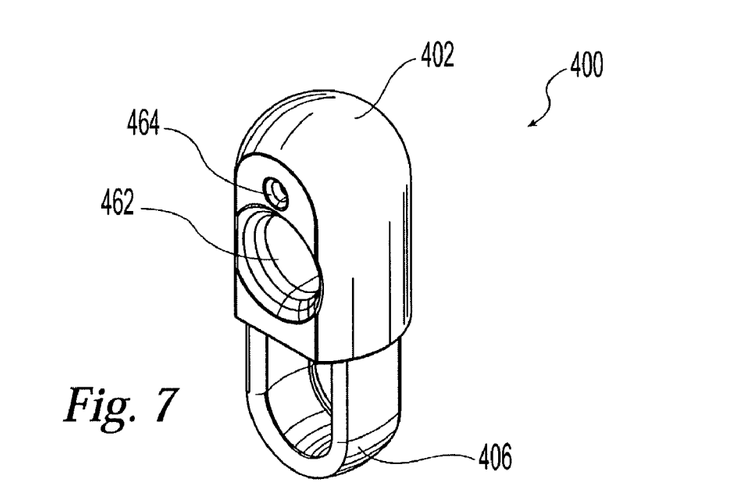
FIG. 7 is a perspective view of the graft block of FIG. 6.

FIGS. 6 and 7 illustrate an alternative embodiment of the graft block of FIG. 1 having a multi-piece construction. A graft block 400 comprises a cap 402, a core 404, and an intermediate connecting member 406 in the form of a loop.

The core 404 includes a rectilinear body having a proximal end 408, a distal end 410, a pair of opposed parallel faces 412 and 414, and a pair of opposed parallel sides 416 and 418. Large 420 and small 422 transverse apertures extend through the body between the faces 412 and 414. The large 420 aperture is proximal of the small aperture 422 and includes a chamfer 423. A pair of projecting side walls 424 and 426 defines a U-shaped channel 428 along the exterior of the core 404 around the distal end and down the parallel sides 416 and 418. The intermediate connecting member 406 comprises a closed elongated loop having a proximal portion 430, a distal portion 432, and sides 434 and 436. The cap 402 includes a hollow rectilinear body having an open proximal end 450, a closed distal end 452, opposite parallel faces 454 and 456, and opposite parallel sides 458 and 460. Large 462 and small 464 transverse apertures extend through both faces 454 and 456. Chamfers 466 and 467 lead from each face 454 and 456 to the large 462 and small 464 apertures. The graft block 400 is assembled by placing the intermediate connector 406 on the core 404 within the U-shaped channel 428 with the distal portion 432 resting on the distal end 410 of the core 404 and the proximal portion 430 extending below the core. The core/connector assembly is inserted through the open proximal end 450 of the cap 402 until the distal end 410 of the core 404 is adjacent the distal end 452 of the cap 402 and the large 420 and small 422 core apertures align with the large 462 and small 464 cap apertures. The assembly may be secured by press fit, snap fit, adhesives, welding, solvent bonding, pinning, screwing, and/or other suitable means. Alternatively, the cap 402 can be molded over the core 404 and intermediate connector 406 or the cap 402 and core 404 can be molded as a single piece around the intermediate connector 406. When fully assembled, the cap covers the distal end 432 and sides 434 and 436 of the intermediate connector 406 such that it is securely retained and protected.

Figure 8:
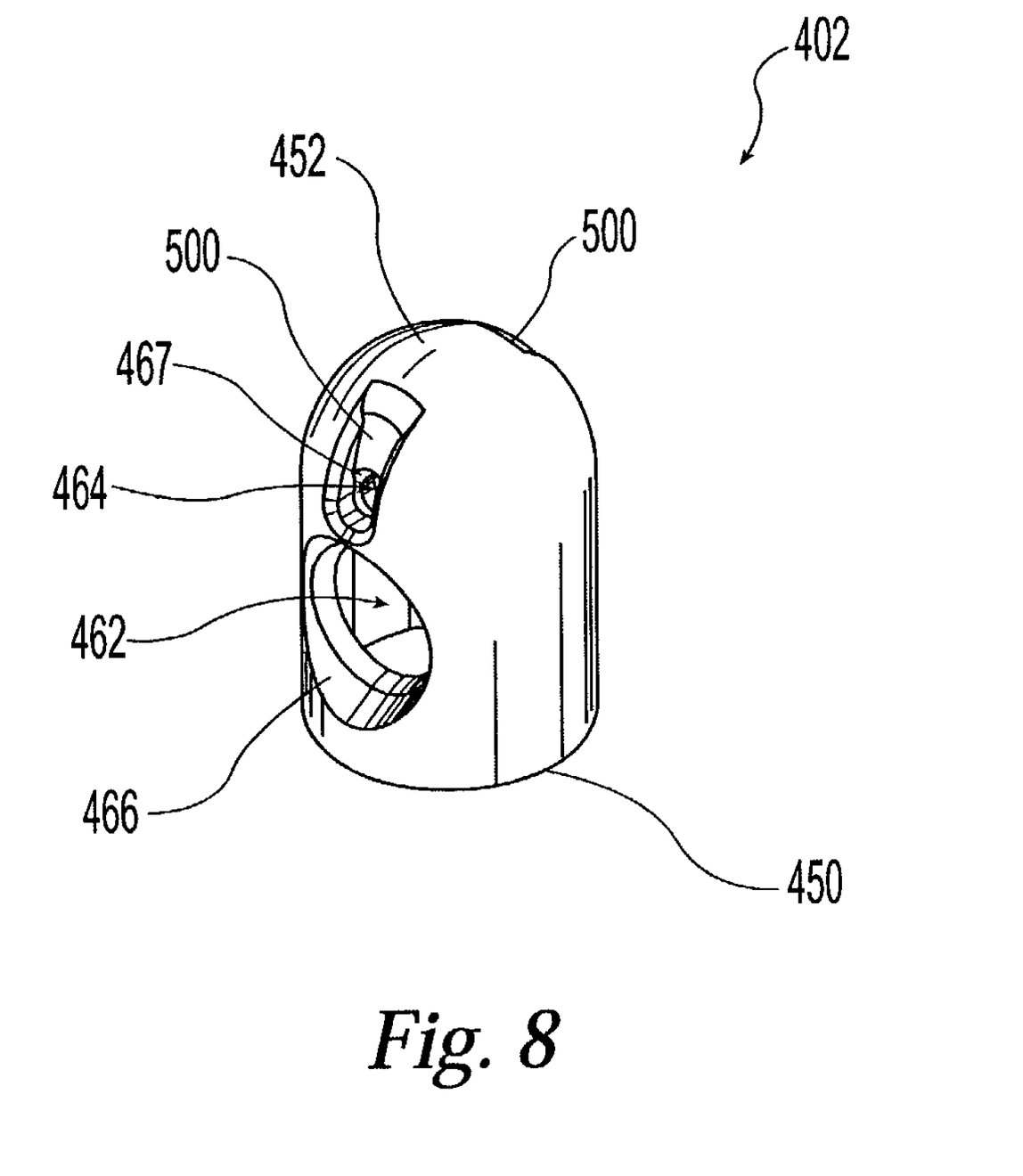
FIG. 8 is a perspective view of an alternative cap used in conjunction with the graft block of FIG. 6.

FIG. 8 depicts an alternative cap 402 having a cylindrical body without the faces 454 and 456 of FIG. 6. A pair of channels 500 lead from each end of the small aperture 464 toward the distal end 452 of the cap 402. The channels 500 receive the passing suture 65 to provide clearance between the cap 402 and bone tunnel.

In addition to the advantages already stated, the present invention offers other advantages in connecting grafts to bone. One such advantage is that the graft block may be configured to enable the surgeon to pull straight on the end of the graft in order to draw it into the bone tunnel. This pulling direction provides the greatest leverage. The ability to pull straight on the graft in a direction aligned with the graft enables the surgeon to form the bone tunnel with as small a diameter as possible in order to produce a more intimate fit between the graft and the wall of the bone tunnel.

Another advantage of the invention is that the large pin receiving aperture enables the placement of a transverse pin through the graft block in one step and without a guide wire or the need for X-ray visualization.

Another advantage of the invention is that it permits delicate handling of the graft and its secure attachment to the graft block outside of the body where it can be visualized and handled with ease. The blind attachment of the graft block/graft assembly within the bone tunnel involves connecting two easily manipulated, robust, positively engaging pieces with little chance for damage to the graft or a partial attachment.

It will be understood by those skilled in the art that numerous improvements and modifications may be made to the preferred embodiment of the invention disclosed herein without departing from the spirit and scope thereof.

What is claimed is:

1. A graft retaining system for retaining a graft in a bone tunnel having a length, a longitudinal axis, an entrance aperture and a closed end, the graft retaining system comprising:
- a graft block having a proximal end, a distal end, and a longitudinal axis extending therebetween, said graft block having an outer side wall, said graft block being sized and adapted to fit within said bone tunnel with its proximal end closer to said entrance aperture and its distal end closer to said closed end, said graft block defining a transverse hole through the graft block transverse to the longitudinal axis and between the proximal and distal ends, the transverse hole having a first end opening to the outer side wall and a second end opening to the outer side wall, the transverse hole having a transverse hole length from the first end to the second end;
- an intermediate connector attached to the graft block, connecting a predetermined portion of said graft, said predetermined portion being situated within said tunnel proximal to said proximal end of said graft block, to a predetermined portion of said graft block at the distal end of said graft block and distal to said transverse hole; and
- an elongated transverse member intraoperatively receivable in said transverse hole to engage bone adjacent said graft block to attach said graft block adjacent said bone tunnel at a predetermined point along the length of said tunnel, the elongated transverse member having a first end, a second end, and defining a transverse member length from the first end to the second end, the transverse member length being greater than the transverse hole length, the transverse member being intraoperatively receivable in the transverse hole with the transverse member extending from both ends of the transverse hole to extend into bone adjacent the graft block near both the first and second ends of the transverse hole.

2. The graft retaining system of claim 1 wherein said intermediate connector creates, in use, a proximally directed force to compress a predetermined portion of said graft block between said intermediate connector and said transverse member.

3. The graft retaining system of claim 2 wherein said intermediate connector is mounted to said graft block with a portion of said graft block molded around a portion of said intermediate connector to connect said intermediate connector to said graft block.

4. The graft retaining system of claim 1 further comprising means for shielding said intermediate connector from abrasion against said bone tunnel.

5. The graft retaining system of claim 4 wherein said means for shielding comprises diametrically opposed longitudinal channels through said graft block, said intermediate connector being looped through said channels.

6. The graft retaining system of claim 1 wherein said predetermined portion of said graft block comprises a portion distal of the transverse hole and the predetermined portion further comprises a transverse channel distal of the transverse hole receiving said intermediate connector.

7. The graft retaining system of claim 1 wherein said intermediate connector comprises a member looped around a portion of said graft block and extending beyond said proximal end of said graft block to receive said graft.

8. The graft retaining system of claim 1 wherein said intermediate connector comprises a loop of flexible material.

9. The graft retaining system of claim 8 wherein said loop comprises at least one strand of flexible material looped a plurality of times around said predetermined portion of said graft block.

10. The graft retaining system of claim 8 wherein said loop comprises at least one continuous loop.

11. The graft retaining system of claim 8 wherein said loop is formed by at least one process selected from the group consisting of tying, bonding, and forming from a single continuous sheet.

12. The graft retaining system of claim 8 wherein said loop comprises a plurality of filaments.

13. The graft retaining system of claim 12 wherein said filaments are combined by at least one process selected from the group consisting of twisting, braiding, weaving, knitting, and bonding.

14. The graft retaining system of claim 1 wherein said intermediate connector comprises at least one structural element selected from the group consisting of cords, tapes, fabrics, and films.

15. The graft retaining system of claim 1 wherein said transverse member comprises a cross-pin including:
- a distal portion having an axis, a distal end and a proximal end;
- a proximal cylindrical portion having an axis, a distal end, and a proximal end, aligned with said distal portion, said proximal portion comprising a threaded exterior surface and a driving means;
- the proximal portion being mounted to the distal portion in relative rotating relationship and axial force transmitting relationship, said proximal portion being able to rotate about its axis relative to said distal portion.

16. A graft retaining system for retaining a graft in a bone tunnel having a length, a longitudinal axis, an entrance aperture and a closed end, the graft retaining system comprising:
- a graft block having a proximal end, a distal end, and a longitudinal axis extending therebetween, said block being sized and adapted to fit within said bone tunnel with its proximal end closer to said entrance aperture and its distal end closer to said closed end;
- tunnel attachment means for attaching said graft block adjacent said bone tunnel at a predetermined point along the length of said tunnel, said tunnel attachment means being situated transverse to the axis of said bone tunnel, said tunnel attachment means being located proximally of said distal end of said graft block; and
- graft attachment means for connecting said graft to said graft block at a position distal to said tunnel attachment means, the graft attachment means producing, in use when operatively attached to said graft, a proximally directed force to compress that portion of said graft block between said graft attachment means and said tunnel attachment means.

17. The graft retaining system of claim 16 wherein said tunnel attachment means comprises a transverse opening formed through said graft block and a transverse member engaging said transverse opening and said bone tunnel, said graft attachment means comprising a portion of said graft attached to said graft block distal of said transverse opening.

18. The graft retaining system of claim 16 wherein said tunnel attachment means comprises a transverse opening formed through said graft block and a transverse member engaging said transverse opening and said bone tunnel, said graft attachment means comprising a portion of said graft looped around a portion of said graft block distal of said transverse opening.

19. The graft retaining system of claim 16 wherein said tunnel attachment means comprises a transverse opening formed through said graft block and a transverse member engaging said transverse opening and said bone tunnel, and said graft attachment means comprises an intermediate connector attached to a portion of said graft and attached to a portion of said graft block distal of said transverse opening.

20. An implantable graft retaining system for retaining a graft in a bone tunnel having a length, an entrance aperture and a closed end, the graft retaining system comprising:
   a graft block implantable within said bone tunnel having a proximal end, a distal end, and a longitudinal axis extending therebetween, said graft block being sized and adapted to fit within said bone tunnel with its proximal end closer to said entrance aperture and its distal end closer to said closed end;
   a transverse pin intraoperatively insertable through said graft block, proximally of said distal end of said graft block, and into bone surrounding the graft block to attach said graft block within said bone tunnel at a predetermined point along said length of said tunnel, the transverse pin blocking withdrawal of the graft block from said bone tunnel; and
   a flexible loop mounted contiguously to said graft block at said distal end and distal to said transverse pin and extending from said graft block toward said entrance aperture, said flexible loop extending away from said proximal end of said graft block a predetermined amount sufficient to enable said loop to receive said graft between said loop and said proximal end to thereby attach said graft to said graft block.

21. A graft retaining system for retaining a graft in a bone tunnel having a length, an entrance aperture and a closed end, the graft retaining system comprising:
   a graft block having a proximal end, a distal end, and a longitudinal axis extending therebetween, said block being sized and adapted to fit within said bone tunnel with its proximal end closer to said entrance aperture and its distal end closer to said closed end;
   a transverse pin engageable with said graft block at a predetermined engagement portion on said graft block between its proximal and distal ends to attach said graft block within said bone tunnel at a predetermined point along said length of said tunnel; and
   at least one channel formed on said graft block distal of said predetermined engagement portion for receiving a portion of said graft such that proximally directed tension on said graft results in compressive loading of said graft block between said channel and said transverse pin.

22. A graft retaining system for retaining a graft in a bone tunnel having a length, an entrance aperture and a closed end, the graft retaining system comprising:
   a graft block having a body having a proximal end, a distal end, a longitudinal axis extending therebetween, and a pair of opposed longitudinal side surfaces, said block being sized and adapted to fit within said bone tunnel with its proximal end closer to said entrance aperture and its distal end closer to said closed end;
   a transverse pin engageable with said graft block at a predetermined engagement portion on said graft block between its proximal and distal ends to attach said graft block within said bone tunnel at a predetermined point along said length of said tunnel;
   a flexible loop adapted to engage both said graft block and said graft; and
   at least one channel formed on said graft block distal of said predetermined engagement portion for receiving a portion of said flexible loop, said flexible loop producing, as a result of a proximally directed tensile load, a compressive force on that portion of said graft block between said channel and said transverse pin.

23. The graft retaining system of claim 22 wherein said at least one channel comprises a pair of opposed and parallel channels extending within said body from said proximal end to said distal end, parallel to said side surfaces and on diametrically opposed sides of said pin receiving aperture, said channels adapted to receive therethrough said flexible loop.

24. The graft retaining system of claim 22 further comprising a longitudinally aligned projection extending from one of said side surfaces.

25. The graft retaining system of claim 22 wherein said body further comprises a pair of opposed and parallel planar face surfaces extending between said proximal and distal ends, said pair of opposed side surfaces joining said planar face surfaces and extending between said proximal and distal ends, wherein said pin is receivable in an aperture extending transversely through said body between said planar face surfaces.

26. The graft retaining system of claim 25 wherein said side surfaces are symmetrical and partially cylindrical, each side surface being curved about an axis parallel to said planar surfaces and extending between said proximal and distal ends.

27. The graft retaining system of claim 22 wherein said transverse pin is able to be advanced into and secured in bone transversely to said bone tunnel, said transverse pin comprising:
   an elongated body having a proximal end and a distal end, said body comprising a pointed tip at said distal end and an axially aligned non-circular drive recess at said proximal end, said body further comprising:
   a first radially outwardly tapered section extending proximally from said distal tip;
   a first cylindrical section extending proximally from said first tapered section;
   a second radially outwardly tapered section extending proximally from said first cylindrical section;
   a second cylindrical section extending proximally from said second tapered section to said proximal end; and
   attachment means situated on said second cylindrical section for securing said pin in said bone.

* * * * *